United States Patent
Carter (10) Patent No.: US 9,364,620 B2
(45) Date of Patent: Jun. 14, 2016

(54) GAS DISPENSER FOR DISPENSING ACCURATE DOSES OF THERAPEUTIC GAS FROM A RESERVOIR CONTAINING HIGHLY COMPRESSED THERAPEUTIC GAS

(75) Inventor: Troy A. Carter, Sunnyvale, CA (US)

(73) Assignee: Capnia, Inc., Redwood City, CA (US)

( * ) Notice: Subject to any disclaimer, the term of this patent is extended or adjusted under 35 U.S.C. 154(b) by 348 days.

(21) Appl. No.: 13/150,872

(22) Filed: Jun. 1, 2011

(65) Prior Publication Data

US 2012/0138053 A1    Jun. 7, 2012

Related U.S. Application Data

(60) Provisional application No. 61/350,417, filed on Jun. 1, 2010.

(51) Int. Cl.

| | |
|---|---|
| *A61M 11/00* | (2006.01) |
| *A61M 15/00* | (2006.01) |
| *A61M 16/20* | (2006.01) |
| *A61M 16/10* | (2006.01) |
| *A61M 15/08* | (2006.01) |

(52) U.S. Cl.
CPC ....... *A61M 15/0065* (2013.01); *A61M 15/0035* (2014.02); *A61M 16/107* (2014.02); *A61M 16/20* (2013.01); *A61M 16/202* (2014.02); *A61M 15/08* (2013.01); *A61M 2202/025* (2013.01); *A61M 2202/0208* (2013.01); *A61M 2202/0225* (2013.01); *A61M 2202/0275* (2013.01); *A61M 2205/123* (2013.01); *A61M 2205/50* (2013.01); *A61M 2205/8225* (2013.01)

(58) Field of Classification Search
None
See application file for complete search history.

(56) References Cited

U.S. PATENT DOCUMENTS

| | | | | |
|---|---|---|---|---|
| 2,860,634 | A | * | 11/1958 | Duncan et al. ........... 128/205.24 |
| 3,870,072 | A | * | 3/1975 | Lindemann .................. 137/557 |
| 4,207,887 | A | | 6/1980 | Hiltebrandt et al. |
| 5,360,396 | A | | 11/1994 | Chan |
| 5,423,741 | A | * | 6/1995 | Frank ............................. 604/26 |
| 5,515,860 | A | * | 5/1996 | Aviv et al. ..................... 600/560 |
| 5,573,005 | A | * | 11/1996 | Ueda et al. .................... 600/543 |
| 5,875,776 | A | * | 3/1999 | Vaghefi .................... 128/203.15 |
| 6,125,844 | A | * | 10/2000 | Samiotes ................. 128/200.23 |

(Continued)

FOREIGN PATENT DOCUMENTS

| | | |
|---|---|---|
| JP | 9-187509 A | 7/1997 |
| JP | 2003-509171 A | 3/2003 |

(Continued)

OTHER PUBLICATIONS

International Search Report mailed on Sep. 16, 2011, for PCT Application No. PCT/US2011/038791, filed on Jun. 1, 2011, two pages.

(Continued)

*Primary Examiner* — Jason Flick
*Assistant Examiner* — Eric Bryant
(74) *Attorney, Agent, or Firm* — Morrison & Foerster LLP (57) ABSTRACT

Devices for intranasally delivering therapeutic gases to a patient. The devices may include a measurement chamber, a combination pressure regulators and a sequencing mechanism that controls valves associated with the pressure regulators. When implemented in a hand-held dispenser, the hand-held dispenser may reliably deliver consistent doses of gas regardless of the unknown state and pressure of the therapeutic gas in the measurement chamber.

8 Claims, 7 Drawing Sheets

(56) References Cited

U.S. PATENT DOCUMENTS

| | | | |
|---|---|---|---|
| 6,581,592 B1* | 6/2003 | Bathe et al. | 128/202.22 |
| 6,959,708 B1 | 11/2005 | Rasor et al. | |
| 7,017,573 B1* | 3/2006 | Rasor et al. | 128/200.24 |
| 7,900,625 B2* | 3/2011 | Kleinstreuer | A61M 15/0086 128/200.14 |
| 2001/0029979 A1* | 10/2001 | Zheng et al. | 137/240 |
| 2002/0144683 A1* | 10/2002 | Gurnee | A61G 10/026 128/205.24 |
| 2004/0129270 A1* | 7/2004 | Fishman | 128/204.18 |
| 2005/0008577 A1* | 1/2005 | Cooper et al. | 424/45 |
| 2005/0028811 A1 | 2/2005 | Nelson et al. | |
| 2005/0085799 A1* | 4/2005 | Luria | A61B 5/6803 606/1 |
| 2006/0283450 A1* | 12/2006 | Shissler et al. | 128/204.21 |
| 2009/0044807 A1* | 2/2009 | Boussignac | 128/205.25 |
| 2009/0188504 A1* | 7/2009 | Siska, Jr. | 128/205.21 |
| 2009/0241953 A1* | 10/2009 | Vandine | A61M 16/204 128/204.21 |

FOREIGN PATENT DOCUMENTS

| | | |
|---|---|---|
| JP | 2004-538027 A | 12/2004 |
| WO | WO-01/03645 A2 | 1/2001 |
| WO | WO-01/03645 A3 | 1/2001 |
| WO | WO-01/21237 A1 | 3/2001 |
| WO | WO-2008/130689 A1 | 10/2008 |
| WO | WO-2011/153261 A1 | 12/2011 |

OTHER PUBLICATIONS

Written Opinion of the International Searching Authority mailed on Sep. 16, 2011, for PCT Application No. PCT/US2011/038791, filed on Jun. 1, 2011, four pages.

* cited by examiner

GAS DISPENSER FOR DISPENSING ACCURATE DOSES OF THERAPEUTIC GAS FROM A RESERVOIR CONTAINING HIGHLY COMPRESSED THERAPEUTIC GAS

CROSS-REFERENCE TO RELATED APPLICATIONS

This application claims priority to U.S. Provisional Application Ser. No. 61/350,417, filed on Jun. 1, 2010, which is hereby incorporated by reference in its entirety.

TECHNICAL FIELD

Described here are devices for dispensing therapeutic gases to the nasal mucosa of a patient. More particularly, the dispensing devices include one or more components for regulating the gas flow and pressure from a hand-held dispenser for the safe, controlled, intranasal delivery of a pressurized therapeutic gas. Methods for intranasally delivering therapeutic gases to patients are also described.

BACKGROUND

A typical compressed gas pressure regulator incorporates a spring-loaded diaphragm mechanism that regulates the opening and closing of a gas discharge orifice. This mechanism can be calibrated manually to provide constant delivery pressure at any value within a designated range. After the desired delivery pressure is set, the regulator may open or close the gas discharge to maintain constant pressure. In turn, the flow rate may be controlled by the use of a separate restricting orifice or similar component. Many different pressure regulating and flow rate controlling features are commercially available. However, these known gas dispensers do not always dispense a therapeutic gas in an accurate and/or economical manner.

Accordingly, dispensers having mechanical and/or functional characteristics that help to optimize the dispensing of therapeutic gases or optimize the delivery of therapeutic gases to target tissues, e.g., the nasal mucosa, would be useful.

SUMMARY

Described here are devices and methods for dispensing therapeutic gases to the nasal mucosa of a patient. In general, the devices are configured to include a compressed gas cylinder, a first valve and a second valve, a first pressure regulator and a second pressure regulator, a measurement chamber that has a defined volume of therapeutic gas at a predetermined pressure set by the first pressure regulator, and a sequencing mechanism that is coupled to the first valve and the second valve. The sequence mechanism may alternately open and close the first valve and second valve. The aforementioned components may be viewed as being operatively connected to each other in a manner that dispenses consistent doses of a therapeutic gas to patients.

In some variations, the compressed gas cylinder is coupled to the input of the first valve, and output of the first valve is coupled to the input on the first pressure regulator, and output of the first pressure regulator is coupled to the input of the second pressure regulator and to the measurement chamber. Here output of the second pressure regulator may be coupled to input of the second valve and output of the second valve may be coupled to the patient. In use, a therapeutic gas typically passes from the compressed gas cylinder through the first pressure regulator to the measurement chamber. The therapeutic gas then passes from the measurement chamber through the second pressure regulator to provide the patient a constant volume of a therapeutic gas.

Variations of the device may further include an orifice to control the rate of gas flow, wherein the output of the second valve is coupled to one end of the orifice and another end of the orifice is coupled to the patient. The sequence mechanism of the devices may comprise either a mechanical or an electronic apparatus.

With respect to the measurement chamber, this component of the device may store a volume of therapeutic gas at a controlled pressure of approximately 200 psi. The patient here may receive a constant flow rate of gas of approximately 0.5 standard liters per minute at a controlled pressure of approximately 1 atmosphere. The therapeutic gases that may be dispensed include without limitation, carbon dioxide, nitric oxide, oxygen, gaseous acids, helium, and combinations thereof.

Methods for intranasally delivering a therapeutic gas to a patient are also described herein. In general, the methods include the steps of obtaining a device comprising a compressed gas cylinder, a first valve and a second valve, a first pressure regulator and a second pressure regulator, a measurement chamber that has a defined volume of therapeutic gas at a predetermined pressure set by the first pressure regulator, and a sequencing mechanism that is coupled to the first valve and the second valve; activating the sequence mechanism to open the first valve and close the second valve to allow the therapeutic gas to flow from the compressed gas cylinder to the measurement chamber; and activating the sequence mechanism to close the first valve and open the second valve to allow the therapeutic gas to flow from the measurement chamber to the patient. The methods are devised so that the patient receives the therapeutic gas at a constant flow rate and pressure.

DETAILED DESCRIPTION

Described here are devices and methods for dispensing therapeutic gases to the nasal mucosa of a patient. The devices typically comprise a combination of a measurement chamber, pressure regulators and a sequencing mechanism that controls valves associated with the pressure regulators. More specifically, the devices are generally configured to include a compressed gas cylinder, a first valve and a second valve, a first pressure regulator and a second pressure regulator, a measurement chamber that has a defined volume of therapeutic gas at a predetermined pressure set by the first pressure regulator, and a sequencing mechanism that is coupled to the first valve and the second valve. When the devices described herein are implemented in a hand-held dispenser, the handheld dispenser may reliably deliver consistent doses of gas regardless of the unknown state and pressure of the therapeutic gas. An additional benefit of the herein described devices is that they may be constructed from inexpensive mechanical components and may be manufactured in a very compact form.

Figure 1:
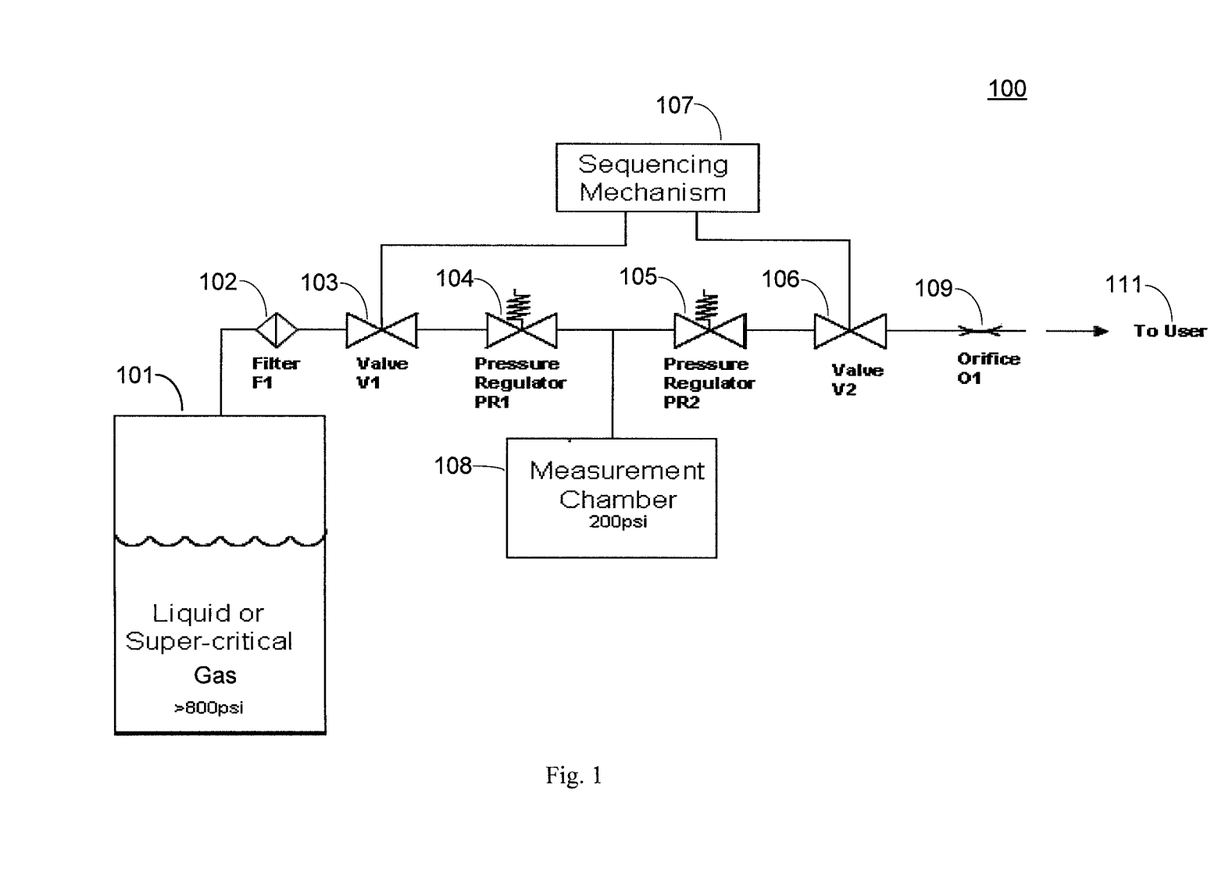
FIG. 1 schematically illustrates the components of an exemplary therapeutic gas dispenser.

An exemplary device 100 is shown in FIG. 1. As shown, device 100 comprises:
1. A standard-sized pressure vessel or compressed gas cylinder 101 that may be filled with liquid or super-critical carbon dioxide or other therapeutic gas and a metallic seal that remains intact until the user activates the device.
2. A mechanism to attach and seal the cylinder to the device.
3. A mechanism for piercing the pressure vessel seal.
4. A filter 102 that prevents particles from passing from the cylinder into the device. The compressed gas cylinder 101 is coupled to the input of the filter 102 and the output of the filter 102 is coupled to the input of the first valve 103.
5. A "primary" or first pressure regulator 104 that reduces the pressure of the carbon dioxide to a set value after it leaves the compressed gas cylinder 101. The output of first valve 103 is coupled to the input of "primary" or first pressure regulator 104.
6. A volumetric chamber or measurement chamber 108 that is filled with the gas at a controlled pressure set by the primary or first pressure regulator 104. The measurement chamber 108 determines or has a defined volume of therapeutic gas at a predetermined pressure set by the first pressure regulator 104.
7. A "secondary" or second pressure regulator 105 that reduces the pressure of the gas to a set value as it exits the measurement chamber 108.
8. An orifice 109 that provides a set flow rate, or rate of gas flow, with the input pressure provided by the second pressure regulator 105.
9. A user interface mechanism or a sequencing mechanism 107 that allows the user to sequentially operate the two valves, first valve 103 and second valve 106, to deliver a measured dose of gas. Specifically, the sequencing mechanism is coupled to the first valve 103 and the second valve 106, wherein the sequencing mechanism 107 alternately opens and closes the first valve and second valve. The output of the second valve 106 is coupled to one end of the orifice 109 and the other end of the orifice 109 is coupled to the user 111 or patient.
10. A nosepiece for user 111 that seals against the user's nostril while gas is dispensed.

In FIG. 1, the device is configured so that the compressed gas cylinder 101 is coupled to the input of the first valve 103, the output of the first valve 103 is coupled to the input on the first pressure regulator 104, and the output of the first pressure regulator 104 is coupled to the input of the second pressure regulator 105 and to the measurement chamber 108.

Further, as shown in FIG. 1, the output of the second pressure regulator 105 is coupled to the input of the second valve 106, and the output of the second valve 106 is coupled to the orifice 109. Orifice 109 is coupled to user 111. The therapeutic gas passes from the measurement chamber 108 through the second pressure regulator 105 and orifice 109 to provide user 111 a constant volume of therapeutic gas.

The devices described herein may be configured as handheld devices that deliver accurately controlled doses of carbon dioxide or other therapeutic gas into a user's nasal passages (to contact the nasal surface, nasal membrane, nasal mucosa, etc.) for medical purposes. The devices generally deliver multiple doses from a single pressurized vessel of carbon dioxide or other therapeutic gas, and each dose may be delivered at a fixed flow rate.

The size of the doses must generally remain relatively constant when operated over a temperature range of about 10-40° C. Because the critical temperature of carbon dioxide is approximately 31° C. (i.e., within the device operating range), the state and pressure inside the cylinder is unknown. As a result, delivering controlled doses of gas from the vessel over this temperature range may be challenging. The physical state of the $CO_2$ in the vessel can be saturated liquid, super-critical fluid or pressurized gas. The corresponding cylinder pressure can range from ~600 psi to ~2000 psi depending on the temperature and quantity of carbon dioxide in the cylinder. See Appendix B.

In some variations, to withdraw a dose of carbon dioxide or other therapeutic gas from a vessel of unknown state, the gas may pass through a pressure regulator and fill a volumetric or measurement chamber at a controlled pressure of approximately 200 psi. This technique of filling a volumetric chamber to a controlled pressure may allow the device to withdraw accurate, repeatable doses of gas from the vessel. To deliver the dose to the patient, the gas may be released from the measurement chamber, and passed through a second pressure regulator (reducing the pressure to approximately 1 atmosphere), and then passed through a 0.005" (0.013 cm) diameter orifice and into the nosepiece. The orifice provides a constant 8 psi pressure drop and generates a relatively constant flow rate of gas of approximately 0.5 standard liters per minute.

FIG. 1 shows a schematic representation of the dose measurement and delivery system that comprise an exemplary gas dispenser. The sequencing mechanism 107 controls the valve action and timing, and may take a variety of forms. The sequencing mechanism 107 may be based on strictly mechanical elements, or may employ microprocessor and electrical actuators to control the valves. That is, the sequencing mechanism 107 may be either a mechanical or an electronic apparatus.

In FIG. 1, the exemplary sequence of events for measuring and delivering a dose are as follows:
1. In the default, or "Ready" state, first valve 103 is closed and second valve 106 is open. First valve prevents the therapeutic gas from exiting the compressed gas cylinder 101. Keeping second valve 106 open prevents pressure from building in the measurement chamber 108 due to leakage through first valve 103.
2. Second valve 106 is closed
3. First valve 103 is opened, allowing the therapeutic gas to flow through filter 102 to the first pressure regulator 104. The therapeutic gas flows through the first pressure regulator 104, filling up the measurement chamber 108 until the designated chamber pressure is reached, at which point the first pressure regulator 104 stops the flow of the therapeutic gas.
4. First valve 103 is closed.
5. Second valve 106 is opened, allowing the therapeutic gas to flow from the measurement chamber 108 through the second pressure regulator 105 and through orifice 109. The second pressure regulator 105 supplies a relatively constant pressure to the orifice 109, which results in a constant flow of the therapeutic gas leaving the orifice 109 and being delivered to user 111.
6. Once the measurement chamber 108 is empty, the system is once again in the default "Ready" state.

Hence, the therapeutic gas passes from the compressed gas cylinder 101 through the first pressure regulator 104 to the measurement chamber 108, and then the therapeutic gas passes from the measurement chamber 108 through the second pressure regulator 105 to provide the user 111 or patient a constant volume of therapeutic gas.

In practical implementations of the device, various components, as illustrated in FIG. 1 may be combined. For example, the functions of the valve and pressure regulators may be integrated into a single unit.

The overall device, e.g., a handheld device, may also include mechanisms to attach the compressed gas cylinder 101, to pierce the seal on the compressed gas cylinder 101, to sequence the operation of the valves in a user-friendly manner, and count the number of doses dispensed from the compressed gas cylinder 101. In addition, the device may include a nosepiece that seals against the user's nostril while a dose is dispensed.

Figure 2:
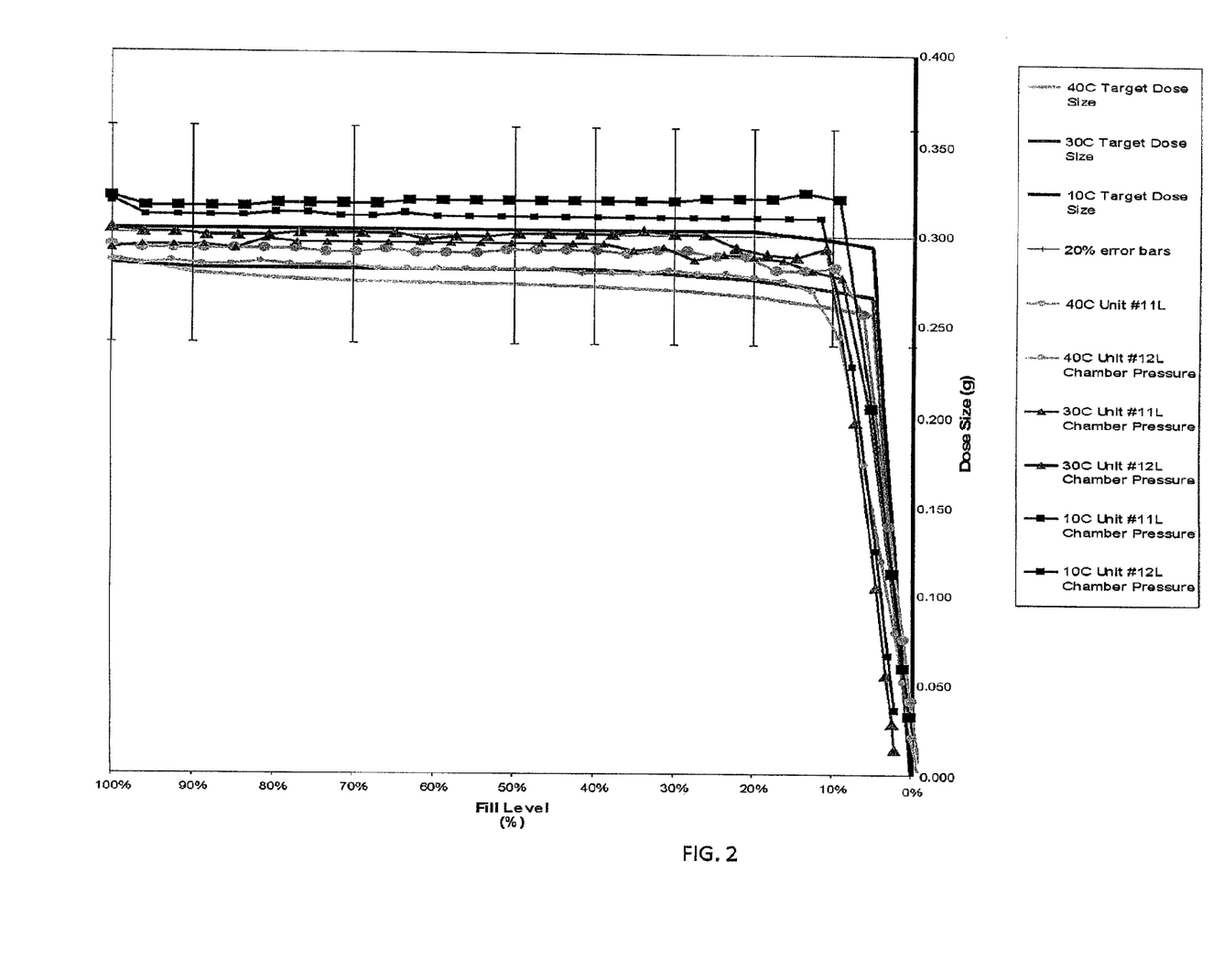
FIG. 2 illustrates an exemplary flow rate performance of a therapeutic gas dispenser.

FIG. 2 illustrates the flow rate performance an exemplary therapeutic gas dispenser. As shown, the flow rate performance is relatively constant for fill levels of the compressed gas cylinder 101 from a fill level of 100% to approximately 10% fill level. Further, the performance is relatively constant over temperatures from 10° C. to 40° C.

Figure 3:
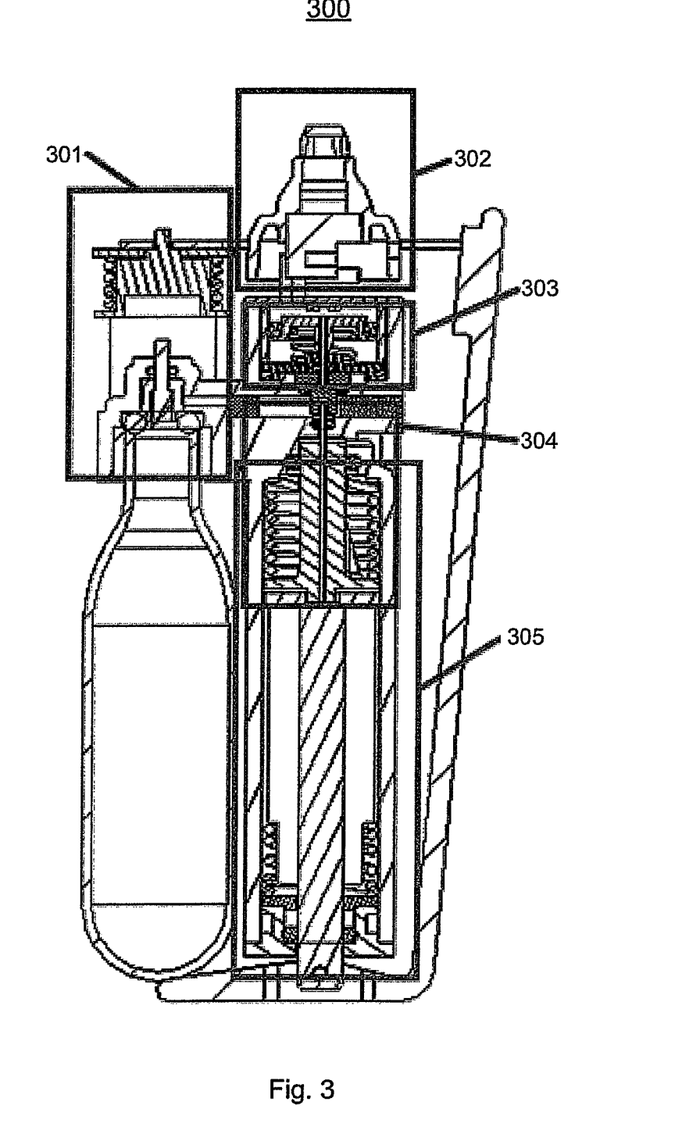
FIG. 3 illustrates the major subsystems of one variation of a therapeutic gas dispenser.

FIG. 3 illustrates details of one variation of the therapeutic gas dispenser, e.g., a hand-held dispenser 300. Shown in FIG. 3 are the cylinder attachment and pierce mechanism 301, the nosepiece 302, the secondary pressure regulator 303, the primary pressure regulator 304, and the measurement chamber 305.

Figure 4:
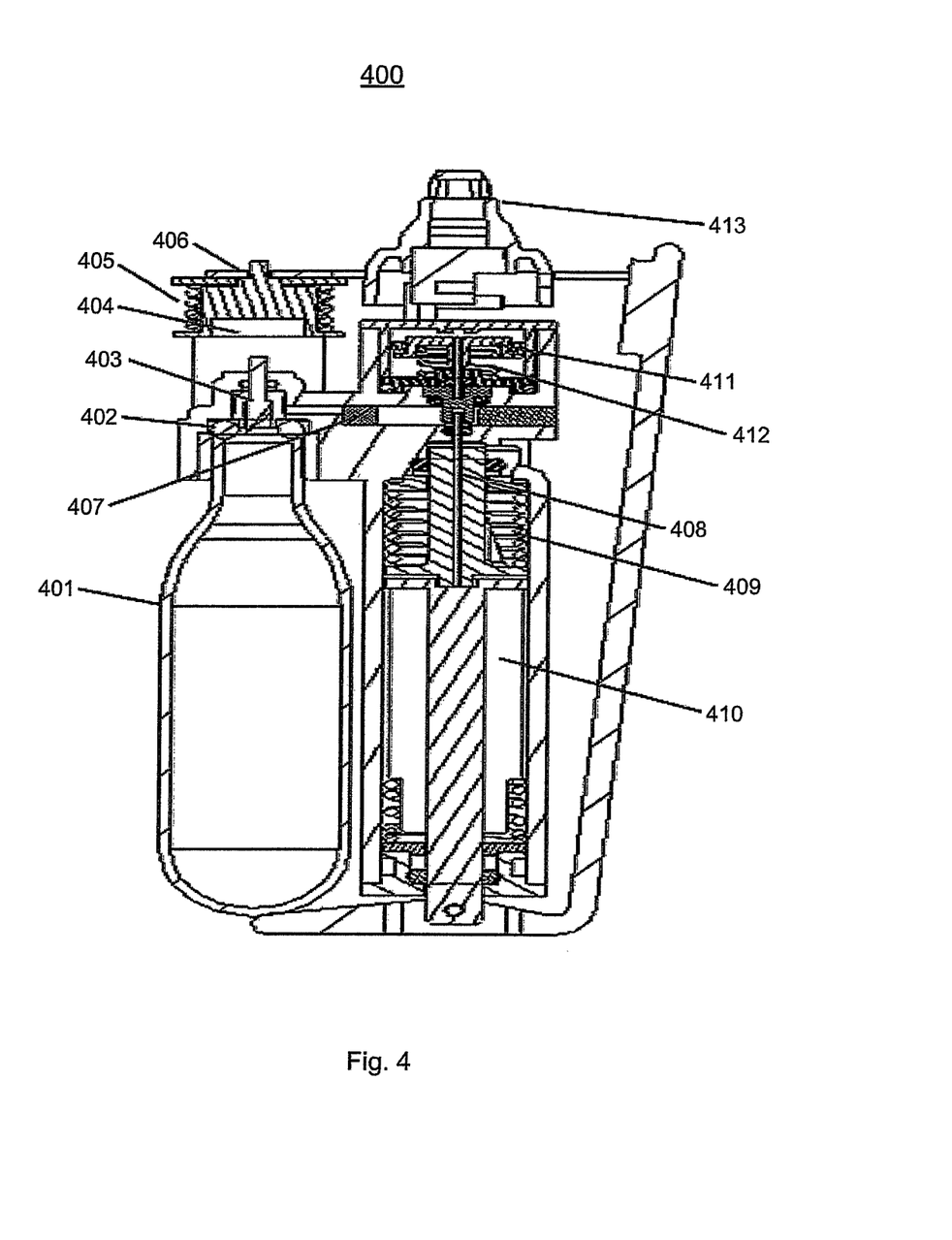
FIG. 4 shows a more detailed view of the dispenser in FIG. 3.

FIG. 4 illustrates further details of the dispenser device 400 shown in FIG. 3 as 300. Shown in FIG. 4 are the following:

1. A standard-sized pressure vessel filled with liquid or super-critical carbon dioxide 401. Multiple doses of carbon dioxide are dispensed from this vessel. The vessel has a metallic seal that remains intact until the user activates the device.
2. A mechanism to attach and seal the cylinder to the device. This mechanism may consist of a threaded port with a face seal that mates against the top of the cylinder 402.
3. A mechanism for piercing the pressure vessel seal. The mechanism may consist of a spring-loaded mass 404 that, when released, drives a pin 403 into the seal. The spring may be a cylindrical coiled spring 405 (as shown in the drawings) or a tapered spring. The tapered spring would be designed to compress flat to reduce the size of the piercing assembly. A clip or pull-tab 406 may secure the assembly until the device is activated.
4. A filter 407 that prevents particles from passing from the cylinder into the device. The filter may consist of a sintered stainless steel frit or sintered plastic. The filter may prevent particles from the pierce pin or the ruptured seal from travelling into the device. The filter also slows the flow of carbon dioxide into the device and creates a significant pressure drop. This pressure drop decreases the chances that liquid or solid carbon dioxide may travel into the device.
5. A "primary" pressure regulator that may reduce the pressure of the carbon dioxide to a set value after it leaves the pressure vessel. In FIG. 4, the primary regulator consists of a spring-loaded piston 408, 409 regulator; alternatively, a number of simple regulator configurations may be used. Examples of applicable pressure regulator configurations are described in Appendix A.
6. A volumetric chamber or measurement chamber 410 may be used to withdraw each dose from the vessel. It is filled with carbon dioxide gas at a pressure set by the primary pressure regulator.
7. A "secondary" pressure regulator that reduces the pressure of the carbon dioxide to a set value as it exits the measurement chamber 410. In FIG. 4, the secondary regulator consists of a spring-loaded piston 411, 412 regulator; alternatively, a number of simple regulator configurations may be used. Examples of applicable pressure regulator configurations are described in Appendix A.
8. An orifice that provides a set flow rate with the input pressure provided by the secondary regulator.
9. A user interface mechanism that allows the user to sequentially operate the two regulators to deliver a measured dose of carbon dioxide gas.
10. A nosepiece 413 that seals against the user's nostril while carbon dioxide is dispensed.

APPENDIX A

Pressure Regulator

As previously stated, the devices described here include pressure regulators and a sequencing mechanism that controls valves associated with the pressure regulators. The described devices configure and functionally implement the pressure regulators in a manner not previously described. Various pressure regulator designs may be employed. This section describes the basic operation of pressure regulators that may be suitable in the therapeutic gas dispensers described herein.

Figure 5:
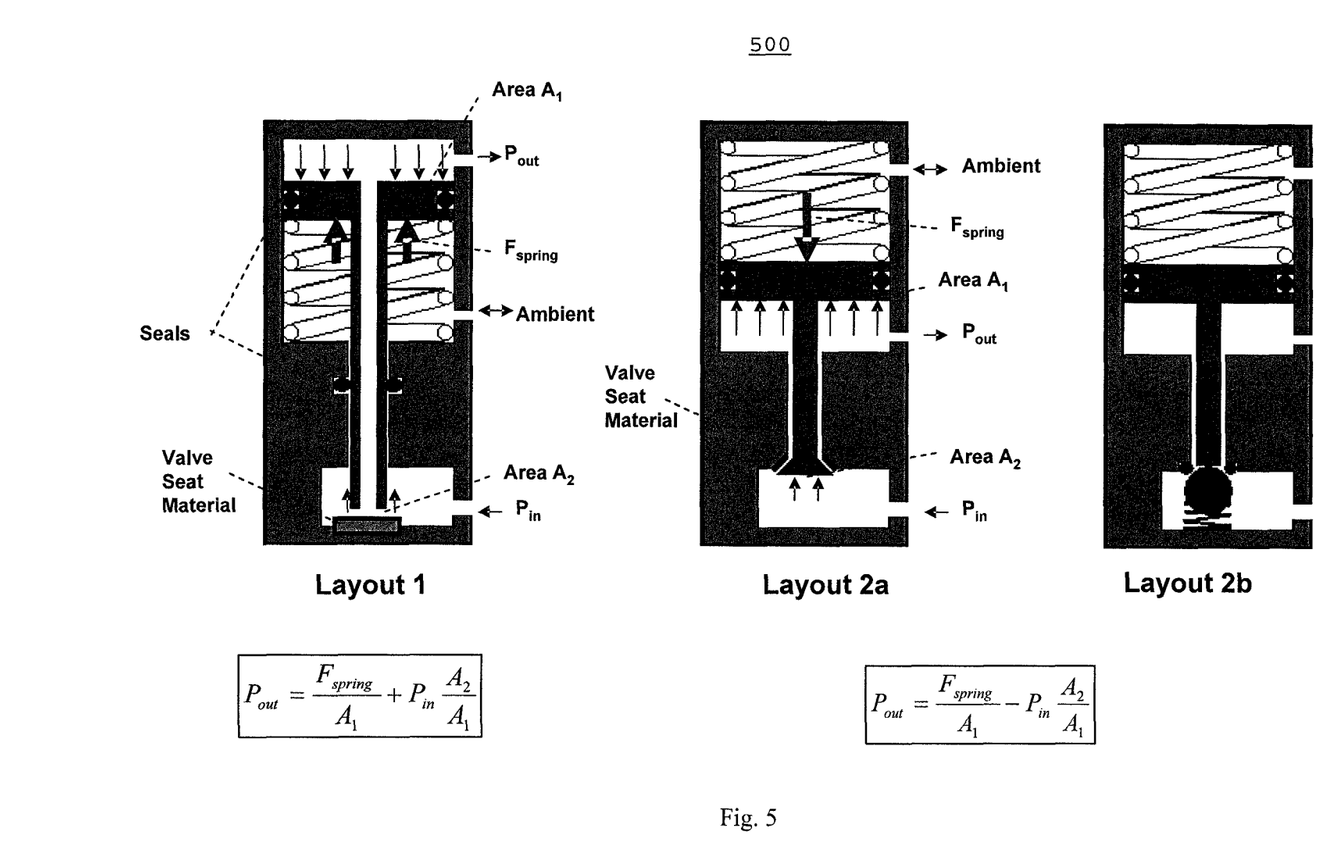
FIG. 5 depicts three layouts of common piston regulators.

FIG. 5 illustrates a number of commonly used "piston regulator" layouts 500 along with the formulas used to predict their behavior. In all configurations, the output pressure $P_{out}$ is dependent on the two areas $A_1$ and $A_2$, the input pressure $P_{in}$, and the spring force acting on the piston when the valve closes. In an ideal regulator, the ratio of the two areas $A_2/A_1$ would be zero. In this case, the output pressure Pout is only dependent on the area A1 and the spring force. In other words, the output pressure is independent of the input pressure.

Besides the mechanical differences, the main difference between layouts 1 and 2*a/b* is their response to changes in input pressure. In layout 1, the output pressure increases with increased input pressure. In layout 2*a/b*, the output pressure decreases with increased input pressure.

In this application, the response characteristics of layout 1 may be preferable to layout 2. Since it is desirable for the measurement chamber to fill with a repeatable mass of carbon dioxide or other therapeutic gas over the expected range of operating temperatures, it is preferable for the measurement chamber pressure to be slightly higher at higher temperatures. Since the input pressure increase at higher temperatures, it may be beneficial to use layout 1. Of course, the ideal regulator output pressure would be constant at all pressures and temperatures.

Figure 6:
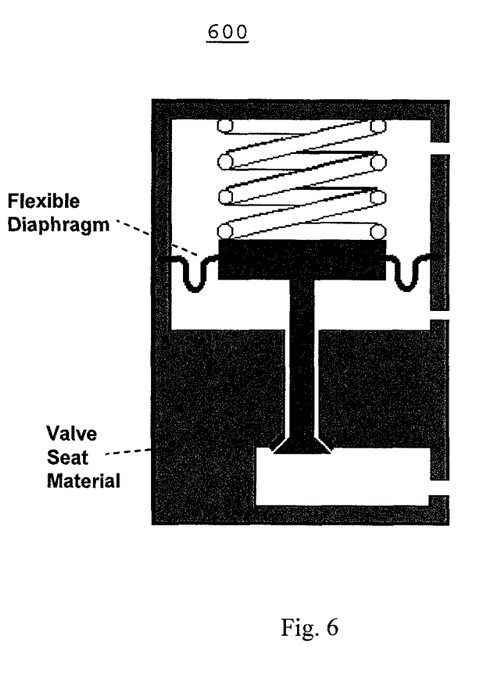
FIG. 6 illustrates a diaphragm regulator analogous to Layout 2a of FIG. 5.

In addition to the piston regulators illustrated above, the devices described here may include analogous regulators 600 that use diaphragms instead of pistons. This concept is illustrated in FIG. 6.

APPENDIX B

Phase Behavior of Carbon Dioxide

One of the important challenges that the devices described here address is the unknown state of the carbon dioxide in the pressure vessel. Over the operating range of 10-40° C., the pressure vessel may contain liquid carbon dioxide and saturated vapor, supercritical carbon dioxide, or carbon dioxide gas. The state depends on the temperature and the amount of carbon dioxide in the vessel. The pressure inside the vessel can range from approximately 600 psi to over 2000 psi depending on the temperature and the amount of carbon dioxide in the vessel.

Figure 7:
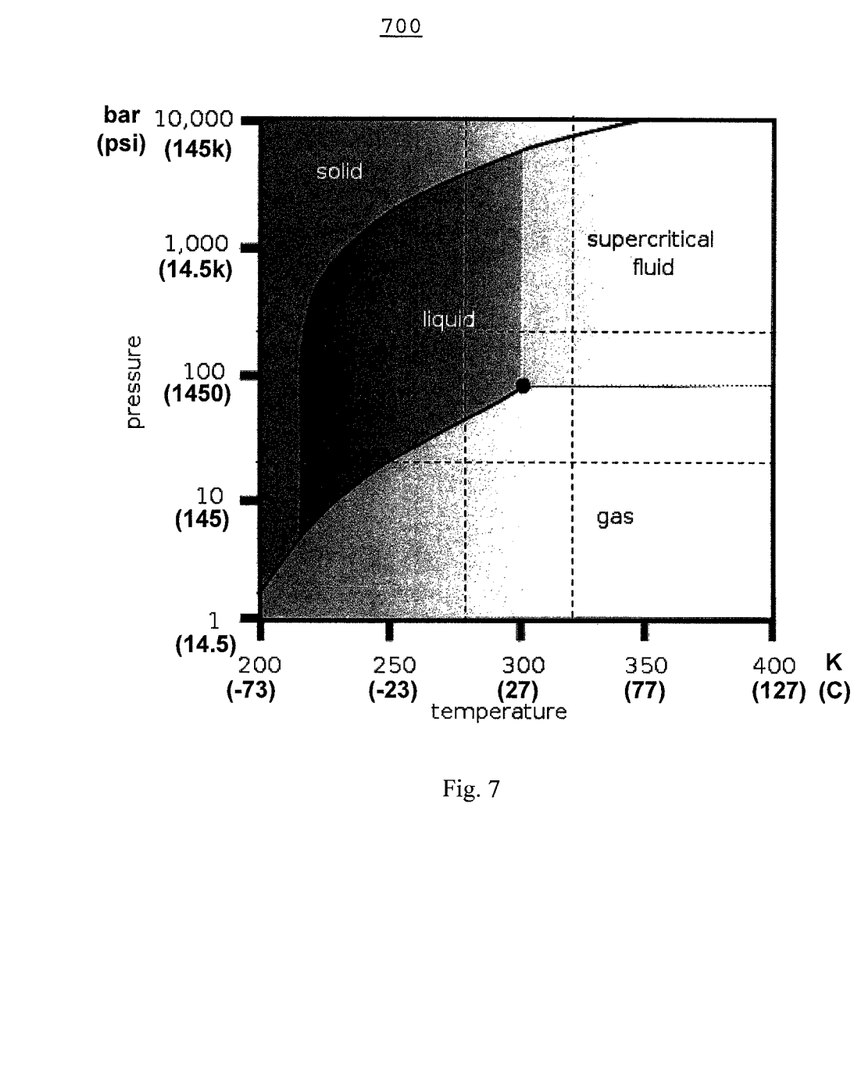
FIG. 7 shows a carbon dioxide phase diagram.

FIG. 7 shows the phase diagram 700 for carbon dioxide. The dotted lines represent the range of temperatures and pressures that may be present in the pressure vessel. The "critical" temperature for carbon dioxide is approximately 31° C. Liquid carbon dioxide cannot exist above this temperature.

The invention claimed is:

1. A hand-held device for intranasally dispensing a repeatable dose of a therapeutic gas to a patient comprising:
   a nosepiece configured to seal against a nostril of the patient,
   a compressed gas cylinder disposed within the hand-held device,
   a first valve and a second valve,
   a first pressure regulator and a second pressure regulator,
   a measurement chamber that has a defined volume of the therapeutic gas at a predetermined pressure set by the first pressure regulator, and
   a sequencing mechanism that is coupled to the first valve and the second valve, wherein the sequence mechanism alternately opens and closes the first valve and second valve,
   wherein the compressed gas cylinder is coupled to input of the first valve, and output of the first valve is coupled to input on the first pressure regulator, and output of the first pressure regulator is coupled to input of the second pressure regulator and to the measurement chamber,
   wherein output of the second pressure regulator is coupled to input of the second valve and output of the second valve is coupled to the patient,
   wherein the therapeutic gas passes from the compressed gas cylinder through the first pressure regulator to the measurement chamber, then the therapeutic gas passes from the measurement chamber through the second pressure regulator and the nosepiece to provide the patient with the repeatable dose of the therapeutic gas at the defined volume.

2. The device as in claim 1, further comprising an orifice to control rate of gas flow, wherein the output of the second valve is coupled to an end of the orifice and another end of the orifice is coupled to the patient.

3. The device as in claim 1, wherein the sequence mechanism is either a mechanical or an electronic apparatus.

4. The device as in claim 1, wherein the therapeutic gas is carbon dioxide.

5. The device as in claim 1, wherein the measurement chamber stores a volume of therapeutic gas at a controlled pressure of approximately 200 psi.

6. The device as in claim 1, wherein the flow rate of the therapeutic gas is approximately 0.5 standard liters per minute.

7. The device as in claim 1, wherein the patient receives the therapeutic gas at a controlled pressure of 1 atmosphere.

8. A method for delivering intranasally a therapeutic gas to a patient comprising the steps of:
   obtaining a hand-held device for intranasally dispensing a repeatable dose of a therapeutic gas to a patient comprising: a nosepiece configured to seal against a nostril of the patient, a compressed gas cylinder disposed within the hand-held device, a first valve and a second valve, a first pressure regulator and a second pressure regulator, a measurement chamber that has a defined volume of the therapeutic gas at a predetermined pressure set by the first pressure regulator, and a sequencing mechanism that is coupled to the first valve and the second valve, wherein the sequence mechanism alternately opens and closes the first valve and second valve, wherein the compressed gas cylinder is coupled to input of the first valve, and output of the first valve is coupled to input on the first pressure regulator, and output of the first pressure regulator is coupled to input of the second pressure regulator and to the measurement chamber, wherein output of the second pressure regulator is coupled to input of the second valve and output of the second valve is coupled to the patient, wherein the therapeutic gas passes from the compressed gas cylinder through the first pressure regulator to the measurement chamber, then the therapeutic gas passes from the measurement chamber through the second pressure regulator and the nosepiece to provide the patient with the repeatable dose of the therapeutic gas at a the defined volume,
   activating the sequence mechanism to open the first valve and close the second valve to allow the therapeutic gas to flow from the compressed gas cylinder to the measurement chamber,
   activating the sequence mechanism to close the first valve and open the second valve to allow the therapeutic gas to flow from the measurement chamber to the patient,
   wherein the patient receives the therapeutic gas at a constant flow rate and pressure.

* * * * *